US006727393B2

(12) United States Patent
Reisinger et al.

(10) Patent No.: US 6,727,393 B2
(45) Date of Patent: Apr. 27, 2004

(54) PROCESS FOR THE PREPARATION OF ORGANIC SOLUTIONS

(75) Inventors: Claus-Peter Reisinger, Wixom, MI (US); Sven Michael Hansen, Leverkusen (DE); Peter Fischer, Köln (DE); Michael Traving, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/319,974

(22) Filed: Dec. 16, 2002

(65) Prior Publication Data

US 2003/0151019 A1 Aug. 14, 2003

(30) Foreign Application Priority Data

Dec. 27, 2001 (DE) ......................... 101 64 142

(51) Int. Cl.⁷ ............................................. C07C 205/00
(52) U.S. Cl. ........................................................ 568/706
(58) Field of Search ................................. 568/706

(56) References Cited

U.S. PATENT DOCUMENTS 3,833,572 A * 9/1974 Clark ........................ 540/217

6,177,538 B1 * 1/2001 Hesse et al. ................ 528/219

FOREIGN PATENT DOCUMENTS

DE   198 58 967    7/2000

OTHER PUBLICATIONS

Analytical Sciences, Feb. 1997, vol. 13, pp. 117–119, "Relationship between the Extractability of Chloro—and Nitrophenolates with Tetrabutylammonium Ion into Chloroform and the Acidity of Their Conjugate Acids" by S. Kusakabe and Y. Anazawa.

Acta Chem. Scand., 23 (month unavailable) 1969, No. 6, pp. 2203–2204 "Ion Pair Extraction in Preparative Organic Chemistry III. Alkylantion of Methyl Cyanoacetate and Related Compounds" by A. Brändström and U. Junggren.

* cited by examiner

Primary Examiner—Michael L. Shippen
(74) Attorney, Agent, or Firm—Joseph C. Gil; Aron Preis

(57) ABSTRACT

A process for the preparation of a solution of a quaternary cation and an anion from a deprotonated hydroxy aromatic in an organic solvent by means of a reactive extraction of a quaternary salt in the presence of an aqueous hydroxide solution, a hydroxy aromatic and an organic solvent is disclosed. Also disclosed is a process for the recycling of a quaternary salt phenolate solution from a reaction mixture.

10 Claims, No Drawings

PROCESS FOR THE PREPARATION OF ORGANIC SOLUTIONS

FIELD OF THE INVENTION

The invention concerns a process for the preparation of organic solutions and in particular solutions containing a quaternary cation and an anion from a deprotonated hydroxy.

SUMMARY OF THE INVENTION

A process for the preparation of a solution of a quaternary cation and an anion from a deprotonated hydroxy aromatic in an organic solvent by means of a reactive extraction of a quaternary salt in the presence of an aqueous hydroxide solution, a hydroxy aromatic and an organic solvent is disclosed. Also disclosed is a process for the recycling of a quaternary salt phenolate solution from a reaction mixture.

BACKGROUND OF THE INVENTION

Salts of quaternary cations and anions from deprotonated hydroxy aromatics, particularly quaternary salt phenolate solutions, may be used in a variety of organic reactions as bases, catalysts or reaction components. Since such salts are not commercially available and their educts are relatively expensive, methods of synthesising these salts and of recovering them from reaction mixtures are required.

DE A 19858967 describes a process for preparing liquid formulations of tetrabutyl ammonium phenolate. Phenolic solutions of tetrabutyl ammonium bromide and sodium phenolate are combined, excess phenol is distilled off and sodium bromide removed by filtration.

The disadvantage of this process is firstly that phenol must be distilled off, requiring a considerable amount of energy, and secondly that the sodium bromide, which may occur as a very finely crystalline deposit, may possibly be difficult to isolate. It is therefore desirable to work out a simpler process that requires less equipment. A further object concerns the recovery of quaternary cation phenolate salts from reaction mixtures. The process should therefore also offer the possibility of reprocessing reaction mixtures in such a way that the quaternary cation phenolate solutions may be recycled.

In working on this object a very simple reactive extraction process was found, with which surprisingly an almost quantitative conversion with surprisingly high extraction yields of organic quaternary salt phenolate solutions are produced, even in a single-stage extraction, with no troublesome by-products.

The invention therefore provides a process for the preparation of organic solutions of salts $(Q^{n+})_k[(^-O)_k-R]_n$ from a quaternary cation $(Q^{n+})$ and a hydroxy aromatic $(R^1-(OH)_k)$, characterised in that an aqueous solution of a hydroxide $M^{r+}(OH^-)_r$, at least one quaternary salt $(Q^{n+})_m[Y^{m-}]_n$, $R^1-(OH)_k$ and at least one solvent that is not completely miscible with water are brought into intimate contact and the aqueous phase is then separated off from the organic phase containing $(Q^{n+})_k[(^-O)_k-R^1]_n$ and optionally $R^1(OH)_k$ and/or $(Q^{n+})_m[Y^{m-}]_n$.

The invention also provides a process for the recovery of quaternary salts from reaction mixtures and their recycling as organic solutions of mixtures of salts $(Q^{n+})_k[(^-O)_k-R^1]_n$ and $(Q^{n+})_m[Y^{m-}]_n$. In the process a mixture that comprise 1. one or more quaternary salts $(Q^{n+})_m[Y^{m-}]_n$
2. a hydroxy aromatic $R^1-(OH)_k$ and optionally
3. one or more organic solvents is reacted as follows:
   a) an aqueous solution of a hydroxide $M^{r+}(OH^-)_r$ and an organic solution containing the quaternary salt $(Q^{n+})_m[Y^{m-}]_n$ are brought into intimate contact and the aqueous phase is then separated from the organic phase containing $(Q^{n+})_k[(^-O)_k-R^1]_n$ and $(Q^{n+})_m[Y^{m-}]_n$ and/or $R^1-(OH)_k$.
   b) The $(Q^{n+})_k[(^-O)_k-R^1]_n$ contained in this organic solution along with the $R^1(OH)_k$ and/or $(Q^{n+})_m[Y^{m-}]_n$ that are optionally present is returned to the reaction after optional additional reprocessing steps.

The present invention also provides a process for the preparation of organic solutions of salts $(Q^{n+})_k[(^-O)_k-R^1]_n$ and $(Q^{n+})_m[Y(1)^{m-}]_n$ from a quaternary cation $(Q^{n+})$ and a hydroxy aromatic $(R^1-(OH)_k)$, characterised in that an aqueous solution of a hydroxide $M^{r+}(OH^-)_r$ having at least two different quaternary salts $(Q^{n+})_m[Y(1)^{m-}]_n$ and $(Q^{n+})_p[Y(2)^{p-}]_n$ and at least one solvent that is not completely miscible with water are brought into intimate contact and the aqueous phase is then separated from the organic phase containing $(Q^{n+})_k[(^-O)_k-R^1]_n$ and $(Q^{n+})_m[Y(1)^{m-}]_n$. $(Q^{n+})_m[Y(1)^{m-}]_n$ and $(Q^{n+})_p[Y(2)^{p-}]_n$ are two different members of the large number of compounds defined by $(Q^{n+})_m[Y^{m-}]_n$, where m and p are natural numbers which may be the same or different. m is preferably smaller than p. Halide $(X^-)$ and sulfate $(SO_4^{2-})$ are a preferred combination of $Y(1)^{m-}$ and $Y(2)^{p-}$, where bromide $(Br^-)$ and sulfate are particularly preferred.

The quaternary salts used in connection with the present invention are typically compounds having the formula $(XR_o^+)_n$, whereby X stands for an atom from group Va or VIa, o for a whole number between 0 and 4 and R mutually independently for $C_6$ to $C_{18}$ aryl, $C_7$ to $C_{18}$ aralkyl or $C_1$ to $C_{20}$ alkyl radicals, and n stands for a natural number.

These include ammonium, guanidinium, phosphonium or sulfonium salts substituted with organic radicals, and optionally also mixtures thereof. The letter n stands for a natural number. Oligomers having n>1 may also be used (in which case (n−1) R radicals act as bridges between two X), but monomeric ions (n=1) are preferred.

Ammonium, guanidinium, phosphonium, sulfonium and sulfoxonium ions having $C_6$ to $C_{18}$ aryl, $C_7$ to $C_{18}$ aralkyl or $C_1$ to $C_{20}$ alkyl radicals as organic radicals are suitable for use in the process according to the invention. The radicals in each case may be all the same or different and may themselves be substituted. Any two substituent radicals may be replaced by a ring, and mixtures of several quaternary cations may optionally also be used.

The following ions may be listed by way of examples: tetramethyl ammonium, tetra-n-ethyl ammonium, tetra-n-propyl ammonium, tetra-n-butyl ammonium, di-n-decyl dimethyl ammonium, di-n-octadecyl dimethyl ammonium, tri-n-decyl methyl ammonium, N-methyl-N-decyl morpholinium, N-methyl methyl pyrrolidinium, N-(2-hydroxyethyl)-N-ethyl piperidinium, benzyl tributyl ammonium, phenyl trimethyl ammonium, tetraphenyl ammonium, tetramethyl phosphonium, tetra-n-ethyl phosphonium, tetra-n-propyl phosphonium, tetra-n-butyl phosphonium, di-n-decyl dimethyl phosphonium, di-n-octadecyl dimethyl phosphonium, tri-n-decyl methyl phosphonium, benzyl tributyl phosphonium, phenyl trimethyl phosphonium, tetraphenyl phosphonium, hexaethyl guanidinium, tetramethyl bishexyl guanidinium.

Tetraalkyl ammonium ions, tetraaryl ammonium ions, tetraalkyl phosphonium ions, tetraaryl phosphonium ions and hexaalkyl guanidinium ions are preferably used. Tetrabutyl or tetraphenyl ammonium ions or tetrabutyl or tetraphenyl phosphonium ions are particularly preferably used, whereby tetrabutyl ammonium ions or tetraphenyl phosphonium ions are most particularly preferably used.

Halides, nitrates, sulfates, hydrogen sulfates, carbonates, hydrogen carbonates, phosphates, hydrogen phosphates, dihydrogen phosphates, tetrafluoroborates, perchlorates, carboxylates or hexafluorophosphates, for example, may be used as the counter-anion $Y^{m-}$ of the quaternary cations. The letter m stands for a natural number. Mixtures of different anions are possible. Halides are preferred, particularly preferably bromide.

Hexaalkyl guanidinium halides, tetraalkyl ammonium halides and tetraaryl phosphonium halides are preferred, whereby tetrabutyl ammonium bromide, tetrabutyl ammonium chloride, tetraphenyl phosphonium bromide and tetrabutyl phosphonium bromide are particularly preferred. The amount of such a quaternary salt may be 0.01 to 30 wt. %, for example, relative to the weight of the reaction mixture. This amount is preferably 0.5 to 15 wt. %, particularly preferably 1 to 5 wt. %.

In the aromatic hydroxyl compounds $R^1$—$(OH)_k R^1$ stands for an aromatic radical and k for a whole number from 0 to 4. These include monohydroxylated aromatic compounds (k=1), dihydroxylated aromatic compounds (k=2), polyhydroxylated aromatic compounds (2<k<=4) and bisphenols (k=2), which may have 0 to 4 substituents including $C_1$–$C_{18}$ alkyl or cycloalkyl, $C_6$–$C_{18}$ aryl, $C_7$–$C_{18}$ aralkyl, $C_1$–$C_{18}$ alkoxy, fluorine, chlorine or bromine. The alkyl, aryl and aralkyl substituents may themselves likewise be substituted or may carry functional groups such as ether, thioether, keto, epoxy groups, halogens, heterocyclic rings. Aromatic substituent rings may be annelated or bridged, and several residual radicals may be combined to form cyclic compounds.

Examples are monohydroxyl compounds such as phenol, o-, m- or p-cresol, o-, m- or p-chlorophenol, o-, m- or p-ethyl phenol, o-, m- or p-propyl phenol, o-, m- or p-tert.-butyl phenol, o-, m- or p-isooctyl phenol, o-, m- or p-stearyl phenol, mesitol, o-, m- or p-phenyl phenol, o-, m- or p-cyclohexyl phenol, o-, m- or p-methoxyphenol, 2,6-dimethyl phenol, 2,4-dimethyl phenol, 3,4-dimethyl phenol, 1-naphthol, 2-naphthol or dihydroxyl or polyhydroxyl compounds such as resorcinol and hydroquinone, and bisphenols such as 2,2-bis-(4-hydroxyphenyl)propane (bisphenol A), 2,2-bis-(3,5-dimethyl-4-hydroxyphenyl)propane, 1,1-bis-(4-hydroxyphenyl)cyclohexane, 1,1-bis-(4-hydroxyphenyl)-3,3,5-trimethyl cyclohexane (bisphenol TMC), -bis-(4-hydroxyphenyl)-m-diisopropyl benzene, 6,6'-dihydroxy-3,3,3',3'-tetramethyl-1,1'-spiro(bis)indane, 4,4'-dihydroxybiphenyl, or 2,4'-dihydroxybiphenyl.

Mixtures of different aromatic hydroxyl compounds may also be used. Monohydroxyl compounds are preferably used, particularly preferably phenol.

Individual substances or mixtures of substances that are only partially miscible with water and are inert with respect to the substances used are utilized as organic solvents. Solvents having a boiling point of between around 40 and 200° C. are preferred. Also preferred are solvents whose dielectric constants are below around 25, particularly preferably solvents having dielectric constants <15. The inert solvent may be contained in the mixture in a proportion of 0 to 99 wt. %, preferably 20 to 98 wt. %, particularly preferably 40 to 98 wt. %, relative to $R^1$—$(OH)_k$. If the amount used is markedly hyperstoichiometric in comparison to the reaction yield, $R^1$—$(OH)_k$ may itself be used as a component of a blend of solvents.

Hydrocarbons, halogenated hydrocarbons and aromatic solvents such as chlorobenzene, dichlorobenzene, fluorobenzene, benzene, toluene, the xylenes, anisole, cyclohexane, petroleum ether, methylene chloride, chloroform or 1,2-dichloroethane, dipolar aprotic solvents such as dimethyl acetamide, acetonitrile, N-methyl pyrrolidone, esters, ethers such as dioxan, tetrahydrofuran, t-butyl methyl ether and etherified glycols, for example, may be used as solvents, particularly preferably chlorobenzene.

$M^{r+}(OH^-)_r$ stands for one or more hydroxides from group Ia (r=1) or IIa (r=2) of the periodic table. Examples are lithium hydroxide, sodium hydroxide, potassium hydroxide, calcium hydroxide. Potassium, sodium and calcium hydroxide are preferred, with sodium hydroxide being particularly preferred. $M^{r+}(OH^-)_r$ may be added to the extraction mixture as an aqueous solution or suspension, alternatively it may be added as a solid together with water, whereby the former is preferred. A process is preferred in which the aqueous phase has a pH of 7 to 14, particularly preferably a pH of around 9 to 13.5, before the extraction is performed.

Embodiments making use of the parameters, compounds, definitions and explanations that are cited as being preferred, particularly preferred or most particularly preferred are preferred, particularly preferred or most particularly preferred.

The definitions, parameters, compounds and explanations cited above in general terms or in preferential ranges may also however be combined with one another in any way, in other words across the individual ranges and preferential ranges.

The manufacturing process according to the invention for $(Q^{n+})_k[(^-O)_k-R^1]_n$ is preferably performed with a molar ratio of $[R^1-(OH)_k]/[M^{r+}(OH^-)_r]$ of greater than around 1.1 [r/k], since surprisingly it was found that a hyperstoichiometric addition of $R^1$—$(OH)_k$ has a positive influence on the yield of the reactive extraction. It is particularly preferably performed with a molar ratio of $[R^1-(OH)_k]/[M^{r+}(OH^-)_r]$ of greater than around 3.1 [r/k].

Depending on the requirements of the organic solutions, around 1 to 99.9% of $(Q^{n+})_m[Y^{m-}]_n$ may be reacted to $(Q^{n+})_k[(^-O)_k-R^1]_n$. Surprisingly it was found that the unreacted $(Q^{n+})_m[Y^{m-}]_n$ may likewise be co-extracted into the organic phase. This may be entirely desirable, for example if $(Q^{n+})_m[Y^{m-}]_n$ acts as a phase transfer catalyst or support electrolyte in a subsequent reaction. The invention therefore also provides organic solutions containing both $(Q^{n+})_k[(^-O)_k-R^1]_n$ and $(Q^{n+})_m[Y^{m-}]_n$.

Depending on the desired ratio of $(Q^{n+})_k[(^-O)_k-R^1]_n$ and $(Q^{n+})_m[Y^{m-}]_n$ in the organic phase, the ratio of hydroxide $M^{r+}(OH^-)_r/(Q^{n+})_m[Y^{m-}]_n$ may be around 0.05 [m/r] to 5 [m/r]. If the ratio is increased, the amount of $(Q^{n+})_k[(^-O)_k-R^1]_n$ that is formed increases, provided that an excess of $R^1$—$(OH)_k$ is present. Surprisingly a ratio of around 1 [m/r] is mostly adequate for an almost complete conversion. Higher ratios then lead to a mostly undesirable higher $M^{r+}$ content in the organic solution.

High $M^{r+}$ contents may be troublesome in industrial processes since the salts containing $M^{r+}$ are generally poorly soluble in organic solution and may precipitate out uncontrollably in reactors.

Surprisingly it was found that the $M^{r+}$ content of the solutions prepared by the process according to the invention is below around 20 ppm. Solutions having an $M^{r+}$ content of below around 10 ppm are preferred, particularly preferably organic solutions having an $M^{r+}$ content of below around 5 ppm. Surprisingly, even in cases where the hydroxide is used hyperstoichiometrically, i.e. $M^{r+}(OH^-)_r/(Q^{n+})_m[Y^{m-}]_n$ greater than around 1 [m/r], no significant amounts of $(M^{r+})_k[(^-O)_k-R]_r$ are extracted into the organic phase.

After extraction the organic solutions obtained are saturated with water according to their water absorption capacity. If they are to be used in reactions in which water has a disruptive effect, they must be dried before use. The processes known to the person skilled in the art, such as e.g. drying over anhydrous salts, stripping, molecular sieves, azeotropic distillation, may be used.

Organic solutions of $(Q^{n+})_k[(^-O)_k—R]_n$ and $(Q^{n+})_m[Y^{m-}]_n$ are required e.g. in the direct carbonylation of phenol with carbon monoxide and oxygen to diphenyl carbonate. The invention therefore provides the use of the organic solutions according to the invention in oxidative carbonylation reactions.

The volume ratios of organic to aqueous phase may be selected within a broad range; for reasons of phase contact and practicality they are not too different; volume ratios of organic to aqueous phase of around 0.01 to 100 are therefore preferred. It has been found that smaller volumes of water have a positive influence on extraction into the organic phase as well as minimising the quantity of waste water. A phase ratio of organic to aqueous phase of around 0.5 to 80 is therefore particularly preferred, most particularly preferably around 2 to 50.

The aqueous phase may contain additional electrolytes, e.g. an alkali or alkaline-earth halide salt. As was surprisingly found, the presence of $(M^{r+})_m(Y^{m-})_r$ may even have a positive influence on the yield of $(Q^{n+})_k[(^-O)_k—R^1]_n$ solutions. A preferred variant is therefore performance in the presence of an additional electrolyte, whereby performance in the presence of a metal salt of the anion $Y^{m-}$ is a particularly preferred variant and performance in the presence of $(M^{r+})_m(Y^{m-})_r$ a most particularly preferred variant.

In the process according to the invention for the reprocessing and recycling of organic solutions of salts $(Q^{n+})_k[(^-O)_k—R^1]_n$ and $(Q^{n+})_m[Y^{m-}]_n$, the commercial availability of e.g. tetrabutyl ammonium bromide may be used for the synthesis of tetrabutyl ammonium phenolate.

In the oxidative direct carbonylation of phenol, tetrabutyl ammonium phenolate for example is used as this phenolate base $(Q^{n+})_k[(^-O)_k—R^1]_n$ and tetrabutyl ammonium bromide as the quaternary salt $(Q^{n+})_m[Y^{m-}]_n$. Since phenolate is consumed during the reaction, e.g. by the carbon dioxide produced as a by-product, or partial or complete protonation may occur during reprocessing steps, a regeneration of the phenolate base $(Q^{n+})_k[(^-O)_k—R^1]_n$ is an important object in this process. A stream formed during reprocessing and generally containing, in addition to other components, unreacted hydroxy aromatic $(R^1—(OH)_k)$, quaternary bromide $(Q^{n+})_m[Y^{m-}]_n$ and a solvent, may be wholly or partially reacted to the quaternary phenolate by the process according to the invention.

The process may be executed in such a way that the stream is divided and only a split stream is wholly or partially reacted for regeneration of the base. Alternatively the entire stream may also be reacted with the quantity of $M^{r+}(OH^-)_r$ required for the desired amount of phenolate. Since surprisingly it was found that especially in a hypostoichiometric state, i.e. with ratios of $M^{r+}(OH^-)_r/(Q^{n+})_m[Y^{m-}]_n$ of below 1 [m/r], the reaction occurs almost quantitatively with the amount of $M^{r+}(OH^-)_r$, the desired amount of quaternary salt phenolate is relatively simple to adjust. The process may then be controlled in such a way that only $(Q^{n+})_m[Y^{m-}]_n$ is added in the reaction feed to compensate for the losses and the losses of $(Q^{n+})_k[(^-O)_k—R^1]_n$ are entirely made up by the reaction according to the invention.

Since after extraction the solutions are saturated with water, it may be useful to dry them in step b) before using them for reactions in which water is disruptive. Other types of reprocessing, such as e.g. removal of the solvent by distillation, isolation of $R^1—(OH)_k$, removal of the residual metal content e.g. by ion exchange or precipitation, evaporation, sedimentation or recrystallisation of the $(Q^{n+})_k[(^-O)_k—R^1]_n$ salts, may likewise occur before recycling back into the reaction.

In step a) an aqueous phase containing the reacted portion of the $Y^{m-}$ is accumulated. If this is a valuable anion such as e.g. $PF_6^-$ or bromide, it may be useful to recover this anion too, e.g. by precipitation, reaction to volatile species and subsequent distillation, evaporation of the solution or other methods.

If the reaction mixture contains partially water-soluble by-products, the process according to the invention may additionally be useful for depleting these components. Furthermore, metal salts such as may be present as catalyst components in the reaction mixture may be separated off into the aqueous phase during this extraction, allowing them to be recovered, which may be useful for ecological or economic reasons. Precipitation methods may also be used to isolate these metal salts. A considerable number of metal ions are precipitated out as hydroxides under the extraction conditions. Precipitations with $Y^{m-}$ or, if $Y^{m-}$ represents anions of polybasic acids, with the $Y^{(m+1)-}$ or $Y^{(m+2)-}$ produced by deprotonation thereof (e.g. $Y^{m-}$=dihydrogen phosphate, m=1, $Y^{(m+1)-}$=hydrogen phosphate, $Y^{(m+2)-}$=phosphate), are also possible and are optionally used for isolating metals. The volume ratios of organic to aqueous phase may be selected within a broad range; for reasons of phase contact and practicality they are not too different; volume ratios of organic to aqueous phase of around 0.01 to 100 are therefore preferred. For the cited reasons a phase ratio of organic to aqueous phase of around 0.5 to 80 is preferred, particularly preferably around 2 to 50.

The aqueous phase may contain additional electrolytes, e.g. an alkali or alkaline-earth halide salt. This may have a positive influence on the yield of $(Q^{n+})_k[(^-O)_k—R^1]_n$ solutions and is therefore a preferred variant. Particularly preferred is the use of $(M^{r+})_m(Y^{m-})_r$, which is also formed as a product, as the additional electrolyte. After extraction the aqueous phase is preferably used in part for the extraction feed stream by being recirculated, or the same aqueous phase is continually used, from which only a purge stream containing $(M^{r+})_m(Y^{m-})_r$ is continually removed and a compensating $M^{r+}(OH^-)_r$ stream added. The distribution equilibria of $R^1(OH)_k$, $(Q^{n+})_m[Y^{m-}]_n$ and $(Q^{n+})_k[(^-O)_k—R^1]_n$ are positively influenced by the resulting hold-up of $(M^{r+})_m(Y^{m-})_r$ in the extraction and losses in the aqueous phase along with the amount of waste water are minimised.

Alternatively the $(M^{r+})_m(Y^{m-})_r$ formed as a product may be separated off as a solid and discharged if the solubility product is exceeded.

The recovery process according to the invention for $(Q^{n+})_k[(^-O)_k—R^1]_n$ is preferably performed with a molar ratio of $[R^1—(OH)_k]/[M^{r+}(OH^-)_r]$ greater than around 1.1 [r/k], since surprisingly it was found that a hyperstoichiometric addition of $R^1—(OH)_k$ has a positive influence on the yield of the reactive extraction. It is particularly preferably performed with a molar ratio of $[R^1—(OH)_k]/[M^{r+}(OH^-)_r]$ greater than around 3.1 [r/k].

The ratio of hydroxide to quaternary salt $M^{r+}(OH^-)_r/(Q^{n+})_m[Y^{m-}]_n$ may be around 0.01 [m/r] to 5 [m/r], depending on the desired ratio of $(Q^{n+})_k[(^-O)_k—R^1]_n$ and $(Q^{n+})_m[Y^{m-}]_n$ in the organic phase. If the ratio is increased, the amount of $(Q^{n+})_k[(^-O)_k—R^1]_n$ that is formed increases, provided that an adequate amount of $R^1—(OH)_k$ is present.

Surprisingly a ratio of around 1 [m/r] is mostly adequate for an almost complete conversion. Ratios of $M^{r+}(OH^-)_r/(Q^{n+})_m[Y^{m-}]_n$ of around 0.1 [m/r] to 1.5 [m/r] are therefore preferred. Higher ratios then lead to a mostly undesirable higher $M^{r+}$ content in the organic solution and to a high loss of $R^1\text{---}(OH)_k$.

The process requires the presence of $R^1\text{---}(OH)_k$ to form the product; excess $R^1\text{---}(OH)_k$ facilitates the preparation of the solutions. Although the process may be used with a large number of reactions, reactions in which $R^1\text{---}(OH)_k$ is used as educt are preferred. Also preferred are reactions in which the reaction product is an organic ester, e.g. an ester of $R^1\text{---}(OH)_k$. Esters of carbonic acid with $R^1\text{---}(OH)_k$, e.g. diphenyl carbonate, are particularly preferred.

Surprisingly it was found for the recovery process according to the invention that the $M^{r+}$ content of the solutions prepared by the process according to the invention is below around 20 ppm. Solutions having an $M^{r+}$ content below around 10 ppm are preferred, particularly preferably organic solutions having an $M^{r+}$ content below around 5 ppm.

The invention thirdly provides a process for the selective preparation of organic solutions of salts $(Q^{n+})_k[(^-O)_k\text{---}R^1]_n$ and $(Q^{n+})_m[Y(1)^{m-}]_n$, since surprisingly it was found that in a mixture of two quaternary salts $(Q^{n+})_m[Y(1)^{m-}]_n$ and $(Q^{n+})_p[Y(2)^{p-}]_n$, $(Q^{n+})_p[Y(2)^{p-}]_n$ may be reacted very selectively with the hydroxide $M^{r+}(OH^-)_r$. $(Q^{n+})_m[Y(1)^{m-}]_n$ and $(Q^{n+})_p[Y(2)^{p-}]_n$ are two different elements from the large number of compounds defined by $(Q^{n+})_m[Y^{m-}]_n$, whereby m and p are natural numbers which may be the same or different. m is preferably smaller than p. Halide (X-) and sulfate ($SO_4^{2-}$) are a preferred combination of $Y(1)^{m-}$ and $Y(2)^{p-}$, whereby bromide (Br-) and sulfate are particularly preferred.

Depending on the selected stoichiometry of the compounds, organic solutions containing $(Q^{n+})_k[(^-O)_k\text{---}R^1]_n$, $(Q^{n+})_m[Y(1)^{m-}]_n$ and $(Q^{n+})_p[Y(2)^{p-}]_n$ may be prepared, whereby the molar ratio of $(Q^{n+})_m[Y(1)^{m-}]_n/(Q^{n+})_p[Y(2)^{p-}]_n$ may significantly increase in comparison to the starting ratio. A further option is to prepare solutions displaying virtually no $(Q^{n+})_p[Y(2)^{p-}]_n$ and composed only of the quaternary salts $(Q^{n+})_k[(^-O)_k\text{---}R^1]_n$ and $(Q^{n+})_m[Y(1)^{m-}]_n$. Almost the entire amount of $(Q^{n+})_m[Y(1)^{m-}]_n$ that is used may be extracted into the organic phase, or part of the $(Q^{n+})_m[Y(1)^{m-}]_n$ may equally be reacted with $M^{r+}(OH^-)_r$ to form $(Q^{n+})_k[(^-O)_k\text{---}R^1]_n$.

The process for the selective preparation of quaternary salt phenolate may also advantageously be used in the reprocessing of reaction mixtures. In reactions requiring an organically soluble bromide source and phenolate base, for example, the loss of phenolate may be compensated by the process according to the invention. This does not require the use of the expensive bromide as educt; instead a sulfate may additionally be added, which reacts selectively to the phenolate without the loss of significant amounts of the bromide source.

The extractions according to the invention may be performed in a single step, in several steps or continuously. Continuous extraction, e.g. countercurrent extraction, is generally preferred.

The preparation or recovery processes according to the invention are performed at a temperature of −10 to 200° C., preferably 10 to 130° C., particularly preferably 20 to 90° C., and under a pressure of 0.1 to 200 bar, preferably 0.5 to 50 bar, particularly preferably 1 to 10 bar.

Extraction processes may be used for the processes according to the invention such as are described for example in KIRK-OTHMER, Encyclopedia of Chemical Technology, Fourth Edition, Volume 10, 1993, pages 125–181 and in Ullmann's Encyclopedia of Industrial Chemistry, Fifth Edition, Volume B3, Unit Operations II, 1988, chapter 6, Liquid—liquid extraction, pages 6–1 to 6–61.

Extraction equipment from the following classification groups may be used to perform the processes according to the invention, such as e.g. columns without energy input, columns with pulsed liquid or pulsed baffles, columns with rotating baffles, mixer-settlers, mixing nozzles and settlers as well as centrifugal extractors.

Examples of columns without energy input that include spray columns, packed columns and sieve-plate columns, which differ in the dispersion of the phases.

Examples of columns with pulsed liquid or pulsed baffles that include pulsed sieve-plate columns, pulsed packed columns, with piston pump, with pulsing devices according to Misek or Wepuko, columns with vibrating sieve plates according to Prochazka or Karr.

Examples of columns with rotating baffles that include the rotating disc contactor (RDC), asymmetric rotating disc extractor (ARD), Oldshue-Rushton multiple-mixer column, Kühni extractor, Scheibel column, SHE extractor and Graesser contactor.

Examples of mixer-settler extractors that include the Davy McKee mixer-settler, Lurgi tower extractor, IMI, General Mills and box-type mixer-settler according to Denver.

Examples of centrifugal extracts that include the Podbielniak centrifugal extractor and the Robatel centrifugal extractor.

The extractors may be operated as single extractors, parallel extractors or as cascades of extractors. If cascades of extractors are used, equipment from one or more classification groups may be operated simultaneously in one cascade. Phase control in a cascade may be performed cocurrently or preferably countercurrently.

It is likewise known to the person skilled in the art that the process depends on the chemical nature of the $R^1\text{---}(OH)_k$, $(Q^{n+})_m[Y^{m-}]_n$ species and of the solvent, and that depending on the distribution coefficient and the desired separation efficiency the extraction must display a suitable number of theoretical separation stages for the specific separation problem and a contact time adjusted to the kinetics of the reactive extraction.

Generally, however, the extraction is preferably performed in a single mixer-settler, since the extraction yield is usually adequate.

EXAMPLES

The extractions are performed by shaking out the phases for around half an hour. After dilution with acetone and internal standard the organic and aqueous phase are then examined by gas chromatography to determine the concentrations of the components. Tetrabutyl ammonium bromide (TBAB,=$(Q^{n+})_m[Y^{m-}]_n$) breaks down in this process into tributylamine and butyl bromide, which are detected. The ratio of tetrabutyl ammonium phenolate (TBAP,=$(Q^{n+})_k[(^-O)_k\text{---}R^1]_n$) to tetrabutyl ammonium bromide may be calculated from the ratio of tributylamine to butyl bromide; the extraction yield into the organic phase is determined from the proportions of tributylamine in the aqueous phase (AP) and organic phase (OP). The concentrations in the tables refer to values before the reactive extraction was performed.

Example 1

31.5 g tetrabutyl ammonium bromide and 15 g phenol in 250 ml chlorobenzene are extracted in a single step at 80° C. with 50 g of an aqueous KOH solution. The results are set out in Table 1.

TABLE 1

| KOH concentration in AP [wt. %] | 5.48 | 6.02 | 6.58 | 7.12 | 8.24 | 10.98 | 16.46 |
|---|---|---|---|---|---|---|---|
| Ratio of KOH/TBAB | 0.5 | 0.55 | 0.6 | 0.65 | 0.75 | 1 | 1.5 |
| Yield of TBAP relative to TBA$^+$ [%] | 49.0 | 54.2 | 55.8 | 60.0 | 61.6 | 69.6 | 95.0 |
| Extraction yield of TBA$^+$ in OP [%] | 97.3 | 97.6 | 97.3 | 97.3 | 97.8 | 97.7 | 98.8 |

Example 2

31.5 g tetrabutyl ammonium bromide and 15 g phenol in 250 ml chlorobenzene are extracted in a single step at 80° C. with 250 g of an aqueous KOH solution. The results are set out in Table 2.

TABLE 2

| KOH concentration in AP [wt. %] | 1.09 | 1.65 |
|---|---|---|
| Ratio of KOH/TBAB | 0.5 | 0.75 |
| Yield of TBAP relative to TBA$^+$ [%] | 36.9 | 61.9 |
| Extraction yield of TBA$^+$ in OP [%] | 73.1 | 71.5 |

Example 3

31.5 g tetrabutyl ammonium bromide and 55 g phenol in 250 ml chlorobenzene are extracted in a single step at 80° C. with 50 g of an aqueous NaOH solution. The results are set out in Table 3.

TABLE 3

| NaOH concentration in AP [wt. %] | 3.92 |
|---|---|
| Ratio of phenol/NaOH | 6 |
| Ratio of NaOH/TBAB | 0.5 |
| Yield of TBAP relative to TBA$^+$ [%] | 51.8 |
| Extraction yield of TBA$^+$ in OP [%] | 100 |

Example 4

18.27 g tetrabutyl ammonium bromide and 381.73 g of a solution of phenol in chlorobenzene are extracted in a single step at 80° C. with 40 and 80 g of an aqueous NaOH solution. The results are set out in Table 4.

TABLE 4

| NaOH concentration in AP [wt. %] | 2.74 | 1.39 | 2.74 | 1.39 |
|---|---|---|---|---|
| Ratio of phenol/NaOH | 25 | 25 | 1 | 1 |
| Ratio of NaOH/TBAB | 0.5 | 0.5 | 0.5 | 0.5 |
| Yield of TBAP relative to TBA$^+$ [%] | 52.9 | 50.0 | 48.6 | 40.8 |
| Extraction yield of TBA$^+$ in OP [%] | 100 | 99.9 | 60.7 | 33.3 |

In all samples the sodium contents in the organic phases are below the detection limit of 5 ppm.

Example 5

18.27 g tetrabutyl ammonium bromide and 66.6 g phenol in 379.1 g chlorobenzene are extracted in a single step at 80° C. with solutions of varying amounts of NaOH and NaBr in 40 g water. The results are set out in Table 5.

TABLE 5

| NaOH concentration in AP [wt. %] | 5.36 | 4.71 | 10.18 | 9.00 | 3.79 | 3.17 | 2.73 |
|---|---|---|---|---|---|---|---|
| NaBr concentration in AP [wt. %] | 0 | 12.1 | 0 | 11.6 | 29.3 | 40.8 | 49.1 |
| Ratio of phenol/NaOH | 12.5 | 12.5 | 6.25 | 6.25 | 12.5 | 12.5 | 12.5 |
| Ratio of NaOH/TBAB | 1 | 1 | 2 | 2 | 1 | 1 | 1 |
| Yield of TBAP relative to TBA$^+$ [%] | 97.0 | 97.6 | 98.9 | 99.4 | 96.6 | 97.7 | 97.5 |
| Extraction yield of TBA$^+$ in OP [%] | 99.9 | 100.0 | 99.9 | 99.9 | 100.0 | 100.0 | 100.0 |
| Sodium content in OP [ppm] | <0.2 | 0.3 | 50 | 110 | 1.4 | 6 | 26 |
| Phenol content in AP [wt. %] | 1.9 | 1.26 | 3.25 | 1.88 | 0.82 | 0.52 | 0.40 |
| Water content in OP [wt. %] | | | | | 0.62 | 0.51 | 0.41 |

Example 6

10.0 g tetrabutyl ammonium bromide, 11.0 g tetrabutyl ammonium sulfate, 90 g chlorobenzene and 20.7 g phenol are extracted at 20° C. with 25.4 g water, to which 1.52 g solid NaOH had been added. The results are summarised in Table 6.

TABLE 6

| NaOH concentration in AP [wt. %] | 5.64 |
|---|---|
| Ratio of phenol/NaOH | 5.8 |
| Ratio of NaOH/TBA$^+$ | 0.55 |
| Ratio of NaOH/(TBA)$_2$SO4 | 2 |
| Yield of TBAP relative to TBA$^+$ [%] | 52.0 |
| "Yield" of TBAB relative to TBA$^+$ [%] | 48.0 |
| Extraction yield of TBA$^+$ in OP [%] | 100 |

With a mass of 128.7 g the organic phase has a sulfate content of 69 mg/kg and a bromide content of 1.8%. The aqueous phase contains 9% sulfate.

Example 7

10.0 g tetrabutyl ammonium bromide, 11.05 g tetrabutyl ammonium sulfate, 90 g chlorobenzene and 10.0 g phenol are extracted at 20° C. with 29 g water, to which 2.76 g solid NaOH had been added. The results are summarised in Table 7.

TABLE 7

| NaOH concentration in AP [wt. %] | 8.69 |
|---|---|
| Ratio of phenol/NaOH | 1.5 |
| Ratio of NaOH/TBA$^+$ | 1.0 |
| Ratio of NaOH/(TBA)$_2$SO4 | 3.63 |
| Yield of TBAP relative to TBA$^+$ [%] | 81.0 |
| "Yield" of TBAB relative to TBA$^+$ [%] | 19.0 |
| Extraction yield of TBA$^+$ in OP [%] | 96.2 |

With a mass of 120.6 g the organic phase has a bromide content of 1.3% and a sulfate content below the detection limit of 0.01%. The aqueous phase has a bromide content of 2.79% and a sulfate content of 5.9%.

Example 1 shows that the yield obtained from the reaction of TBAB to TBAP may be controlled by the amount of hydroxide. Surprisingly the reaction proceeds with virtually a quantitative yield relative to the hydroxide with a ratio of KOH/TBAB=0.5. In a single extraction step both quaternary salts (tetrabutyl ammonium bromide, tetrabutyl ammonium phenolate) may be transferred almost quantitatively to the organic phase.

Example 2 demonstrates that both the reaction to the phenolate and the extraction yields deteriorate dramatically when the phase ratio of the organic to the aqueous phase is changed.

Example 3 and 4 show that both the yield of TBAP relative to the total amount of quaternary ion (TBA$^+$) and the extraction yield increase if the phenol concentration is raised.

Example 5 demonstrates that surprisingly the addition of sodium bromide has no negative influence on the formation of TBAP and that surprisingly the amount of sodium transferred into the organic phase is very small. Conversely, little phenol is surprisingly taken up by the aqueous phase too and surprisingly the water content in the organic phase falls.

Example 6 proves that in the mixture of quaternary sulfates and quaternary bromides it is possible to convert the quaternary sulfate to the phenolate very selectively and to extract it into the organic phase together with the virtually unreacted quaternary bromide by a precise adjustment of the hydroxide stoichiometry.

Example 7 shows that with hydroxide amounts that are hyperstoichiometric relative to the sulfate amount, the bromide may additionally be partly reacted to the phenolate. The reaction and extraction is not quantitative because of the unfavourable phenol/NaOH ratio.

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A process for the preparation of organic solutions comprising

A) mixing (a) an aqueous solution of a hydroxide $M^{r+}(OH^-)_r$, (b) at least one salt conforming to $(Q^{n+})_m[Y^{m-}]_n$, (c) $R^1$—$(OH)_k$ and (d) at least one solvent that is not completely miscible with water to obtain a material system that contains an aqueous phase and an organic phase, the organic phase containing $(Q^{n+})_k[(^-O)_k$—$R^1]_n$ and optionally $R^1(OH)_k$ and/or $(Q^{n+})_m[Y^{m-}]_n$, and B) separating the aqueous phase from the organic phase, where $Q^{n+}$ denotes hexaalkyl guanidinium ion or $(XR_o^+)$, where X is an atom selected from the group consisting of elements of group Va and VIa of the Periodic Table of the Elements, o is a whole number of 1 to 4, R is $C_1$–$C_{18}$ alkyl, $C_1$–$C_{18}$-cycloalkyl, $C_7$–$C_{18}$ aralkyl, $C_6$–$C_{18}$ aryl and any two radicals R may be replaced by a ring, and n and m independently one of the other denote natural numbers, $Y^{m-}$ is at least one member selected from the group consisting of halide, nitrate, sulfate, hydrogen sulfate, phosphate, hydrogen phosphate, dihydrogen phosphate, perchlorate, hydrogen carbonate and carbonate ion, and $R^1$ denotes an aromatic radical and k is a whole number of 0 to 4, and wherein the solvent is inert with respect to the reactive components of said material system, and $M^{r+}(OH^-)_r$ is at least one hydroxide of elements selected from groups Ia and IIa of the Periodic Table of the Elements and r is 1 or 2.

2. A process for the recovery of quaternary salts from a reaction mixture comprising at least one quaternary salt $(Q^{n+})_m[Y^{m-}]_n$ and a hydroxy aromatic R—$(OH)_k$ Comprising a) mixing the reaction mixture and an aqueous solution of a hydroxide $M^{r+}(OH^-)_r$ to form a material system that contains an aqueous phase and an organic phase, and b) separating the aqueous phase and the organic phase, and c) returning the organic phase comprising $(Q^{n+})_k[(^-O)_k$—$R]_{nk}$ and/or $(Q^{n+})_m[Y^{m-}]_n$, optionally after additonal reprocessing steps, to a reaction that entails at least one quaternary salt.

3. A process for the preparation of an organic solution comprising (i) Mixing an aqueous solution of a hydroxide $M^{r+}(OH^-)_r$ with at least two different quaternary salts $(Q^{n+})_m[Y(1)^{m-}]_n$ and $(Q^{n+})_p[Y(2)^{p-}]_n$ and with at least one solvent that is not completely miscible with water, to form a material system that contains an aqueous phase and an organic phase, and (ii) separating the organic phase, wherein the organic phase comprise salts conforming to $(Q^{n+})_k[(^-O)_k$—$R]_n$ and to $(Q^{n+})_m[Y(1)^{m-}]_n$, where $(Q^{n+})$, $Y^{m-}$, $M^{r+}$, r, m, n, R—$(OH)_k$, $(^-O)_k$—R and k have the meanings specified in claim 1 and p denotes a natural number.

4. The process according to claim 1 in which the R—$(OH)_k$ and $M^{r+}(OH^-)$ are present in amounts such that the molar ratio R—$(OH)_k/M^{r+}(OH^-)_r$ is greater than 1.1.

5. The process according to claim 1 in which the molar ratio $M^{r+}(OH^-)_r/(Q^{n+})_m[Y^{m-}]_n$ is 0.05 to 3.

6. The process according to claim 1 in which the content of $M^{r+}$ in the organic solution is below 20 ppm.

7. The process according to claim 1 in which $Q^{n+}$ is at least one member selected from the group consisting of ammonium, phosphonium, guanidinium and sulfonium salts substituted with organic radicals.

8. The process according to claim 2, in which $M^{r+}(OH^-)_r$ denotes NaOH, R—$(OH)_k$ denotes phenol and at least one element corresponds to the $Y^{m-}$ bromide.

9. The process according to claim 1 wherein the material system contains at least one additional electrolyte.

10. The process according to claim 9, in which the content of the additional electrolyte is adjusted by the partial reuse of aqueous extract solution.

* * * * *